Figure 1:
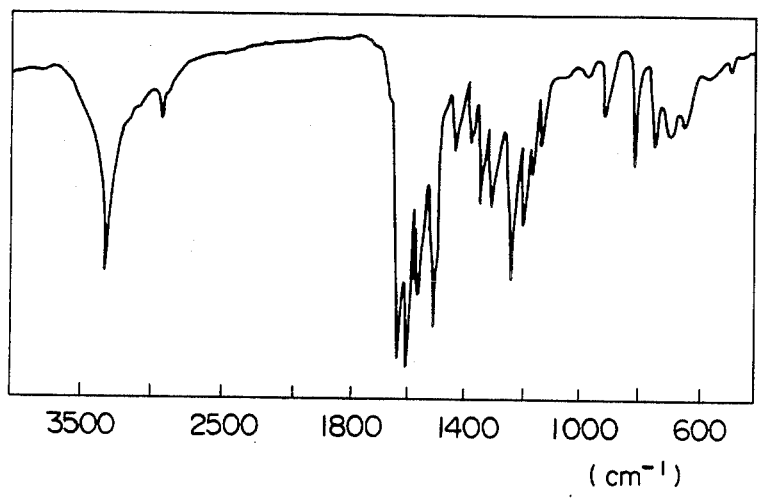

United States Patent [19]

Kato

[11] Patent Number: 4,803,223

[45] Date of Patent: Feb. 7, 1989

[54] SUBSTITUTED AMINOPHENYL UREA DERIVATIVES

[75] Inventor: Shozo Kato, Fujisawa, Japan

[73] Assignee: Tokuyama Soda Kabushiki Kaisha, Yamaguchi, Japan

[21] Appl. No.: 831,266

[22] Filed: Feb. 20, 1986

[30] Foreign Application Priority Data

Feb. 21, 1985 [JP] Japan ................................. 60-31510

[51] Int. Cl.$^4$ ............... C07C 149/437; C07C 127/19; A61K 31/10; A61K 31/17
[52] U.S. Cl. ..................................... 514/521; 514/597; 558/394; 558/395; 564/49; 564/50
[58] Field of Search .................... 564/49, 50; 514/521, 514/597; 558/394, 395; 534/850

[56] References Cited

U.S. PATENT DOCUMENTS

| | | | |
|---|---|---|---|
| 3,138,571 | 6/1964 | Popoff | 564/50 X |
| 3,266,982 | 8/1966 | Popoff | 514/597 X |
| 3,484,484 | 12/1969 | Schwartz et al. | 564/50 |
| 3,637,653 | 1/1972 | von Brachel et al. | 534/850 X |
| 3,803,198 | 4/1974 | Durr | 564/50 X |
| 3,895,061 | 7/1975 | Richter | 564/49 X |
| 3,968,099 | 7/1976 | Leverenz | 534/850 X |
| 4,397,868 | 8/1983 | De Vries | 514/597 X |
| 4,623,662 | 11/1986 | De Vries | 514/597 X |

FOREIGN PATENT DOCUMENTS 292965 9/1969 U.S.S.R. ................................. 564/50

OTHER PUBLICATIONS

Bardos et al., *J. Med. Chem.*, 8, 167–174, (1965).

Primary Examiner—Glennon H. Hollrah
Assistant Examiner—Carolyn S. Greason
Attorney, Agent, or Firm—Sherman and Shalloway

[57] ABSTRACT

A substituted aminophenylurea derivative represented by the general formula

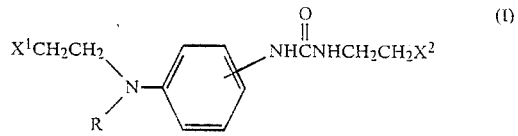

wherein
X$^1$ and X$^2$ are identical or different and each represents a halogen atom, and
R represents a substituted or unsubstituted saturated or unsaturated aliphatic hydrocarbon group, and an acid addition salt thereof, and a process for preparation thereof, the compound of formula (I) being useful as antitumor agent.

22 Claims, 1 Drawing Sheet

SUBSTITUTED AMINOPHENYL UREA DERIVATIVES

This invention relates to novel substituted aminophenylurea derivatives. More specifically, it relates to substituted aminophenylurea derivatives represented by the general formula

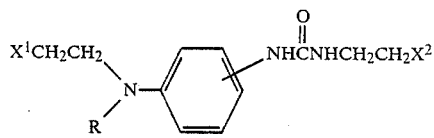

wherein
$X^1$ and $X^2$ are identical or different and each represents a halogen atom, and
R represents a substituted or unsubstituted saturated or unsaturated aliphatic hydrocarbon group,
acid addition salts thereof, a process for production thereof, and to their use as a medicament, particularly an agent useful for the treatment of tumor.

Many compounds having antitumor activity have heretofore been proposed, and some of them have been clinically used as antitumor agents. When the compounds having antitumor activity are classified according to their action, there are a group of compounds called alkylating agents. Generally, the alkylating agents have a haloalkyl group as a functional group in the molecule. Among them, bis(haloethyl)aminobenzene derivatives of the following formula

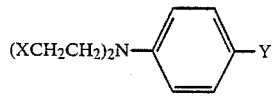

wherein
X is a halogen atom, and
Y is H, COOH, CHO or $NHCOCH_3$,
are particularly actively studied [Journal of Medicinal Chemistry, 8, 167 (1965)]. These bis(haloethyl)aminobenzene derivatives have antitumor activity against several kinds of cancer cells, but their neurotic toxicity and acute toxicity are very strong. Accordingly, side-effects by such strong toxicity preclude clinical use of these compounds as an antitumor agent.

It has been strongly desired therefore to develop an antitumor agent which is safe with low toxicity and little side effects and has an excellent antitumor effect against various kinds of cancer cells.

The compounds of formula (I) provided by this invention meet this desire. The compounds of formula (I) have excellent pharmacological properties, particularly strong antitumor activity, and little toxicity and are useful as medicaments, particularly an antitumor agent.

In the present specification and claims, the "halogen atom" include fluorine, chlorine, bromine and iodine atoms. The term "saturated or unsaturated aliphatic hydrocarbon group" includes open-chain, linear or branched hydrocarbon groups which may have at least one double or triple bond in the chain. Specific examples are alkyl groups such as methyl, ethyl, n- or iso-propyl, n-, iso-, sec- or tert-butyl, n- or iso-pentyl, n-hexyl, n-heptyl, n-octyl, and 2-ethylhexyl; alkenyl groups such as vinyl, allyl, butenyl, pentenyl, hexenyl and octenyl; and alkynyl groups such as ethynyl, propynyl, butynyl, pentynyl and hexynyl. These hydrocarbon groups are preferably "lower". The term "lower", as used herein, means that a group or a compound qualified by this term has up to 6, preferably up to 4, carbon atoms.

The saturated or unsaturated aliphatic hydrocarbon group may be substituted. Examples of the substituent include halogen atoms; alkoxy groups such as methoxy, ethoxy, n-propoxy, iso-propoxy, n-butoxy and tert-butoxy; alkylthio groups such as methylthio, ethylthio, n-propylthio, n-butylthio and sec-butylthio; and aryloxy groups such as phenoxy; and a cyano group. The hydrocarbon group may be substituted by at least one, preferably only one, such substituent. The alkoxy and alkylthio groups are preferably lower, particularly have up to 4 carbon atoms. Examples of the substituted hydrocarbon groups include haloalkyl groups such as chloromethyl, bromomethyl, iodomethyl, fluoromethyl, chloroethyl, bromoethyl, iodoethyl, fluoroethyl, chloropropyl, bromopropyl, chlorobutyl, bromobutyl, chloropentyl, bromopentyl, chlorohexyl and bromohexyl; alkoxyalkyl groups such as methoxymethyl, methoxyethyl, methoxypropyl, methoxypentyl, methoxyhexyl, ethoxymethyl, ethoxyethyl, ethoxypropyl, ethoxybutyl, ethoxypentyl, ethoxyhexyl, propoxymethyl, propoxyethyl, propoxypropyl, propoxybutyl, propoxypentyl, propoxyhexyl, butoxymethyl, butoxyethyl, butoxypropyl, butoxybutyl, butoxypentyl and butoxyhexyl; alkylthioalkyl groups such as methylthiomethyl, methylthioethyl, methoxythiopropyl, methylthiobutyl, methylthiopentyl, methylthiohexyl, ethylthiomethyl, ethylthioethyl, ethylthiopropyl, ethylthiobutyl, ethylthiopentyl, ethylthiohexyl, propylthiomethyl, propylthioethyl, propylthiopropyl, propylthiobutyl, propylthiopentyl, propylthiohexyl, butylthiomethyl, butylthioethyl, butylthiopropyl, butylthiobutyl, butylthiopentyl and butylthiohexyl; phenoxyalkyl groups such as phenoxymethyl, phenoxyethyl, phenoxypropyl, phenoxybutyl, phenoxypentyl and phenoxyhexyl; cyanoalkyl groups such as cyanomethyl, cyanoethyl, cyanopropyl, cyanobutyl, cyanopentyl and cyanohexyl; haloalkenyl groups such as chlorovinyl, bromovinyl, iodovinyl, fluorovinyl, chloroallyl, bromoallyl, iodoallyl, fluoroallyl, chlorobutenyl, bromobutenyl, iodobutenyl, fluorobutenyl, chloropentyl, bromopentenyl, iodopentenyl, fluoropentenyl, chlorohexenyl, bromohexenyl, iodohexenyl and fluorohexenyl; alkoxyalkenyl groups such as methoxyvinyl, ethoxyvinyl, propoxyvinyl, butoxyvinyl, methoxyallyl, ethoxyallyl, propoxyallyl, butoxyallyl, methoxybutenyl, ethoxybutenyl, propoxybutenyl, butoxybutenyl, methoxyhexenyl, ethoxyhexenyl, propoxyhexenyl and butoxyhexenyl; alkylthioalkenyl groups such as methylthiovinyl, ethylthiovinyl, propylthiovinyl, butylthiovinyl, methylthioallyl, ethylthioallyl, propylthioallyl, butylthioallyl, methylthiobutenyl, ethylthiobutenyl, butylthiobutenyl, methylthiopentenyl, ethylthiopentenyl, propylthiopentenyl, butylthiopentenyl, methylthiohexenyl, ethylthiohexenyl, propylthiohexenyl and butylthiohexenyl; phenoxyalkenyl groups such as phenoxyvinyl, phenoxyallyl, phenoxybutenyl, phenoxypentenyl and phenoxyhexenyl; and cyanoalkenyl groups such as cyanovinyl, cyanoallyl, cyanobutenyl, cyanopentenyl and cyanohexenyl.

Preferred substituted or unsubstituted saturated or unsaturated hydrocarbon groups R include lower alkyl groups, lower halo alkyl groups, lower alkoxy lower alkyl groups, lower alkylthio lower alkyl groups, lower phenoxy alkyl groups, lower cyano alkyl groups, lower alkenyl groups, lower halo alkenyl groups, lower alkoxy lower alkenyl groups, lower alkylthio lower alkenyl groups, lower phenoxy alkyl groups, lower cyano alkenyl groups and lower alkynyl groups. From the viewpoint of antitumor activity, lower alkyl groups, an allyl group and lower halo alkyl groups are more preferred. Above all, lower halo alkyl groups, especially haloethyl groups, are preferred.

In formula (I), the moiety

may be present at any of ortho, meta and para positions to the substituted amino group

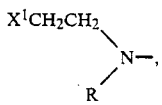

but from the standpoint of the ease of production and pharmaceutical properties, it is most advantageously present at the p-position.

Among the compounds of general formula (I) provided by this invention, bis(haloethyl)aminophenylurea derivatives represented by the following formula

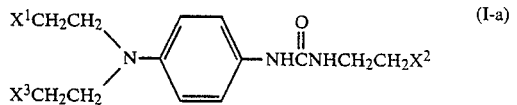

wherin $X^1$, $X^2$ and $X^3$ are identical or different and each represents a halogen atom, are especially preferred.

Typical examples of the compounds of general formula (I) provided by this invention are shown below.

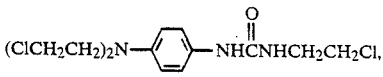

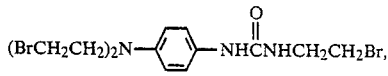

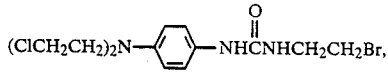

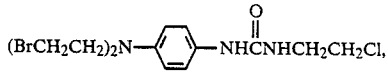

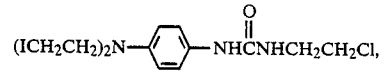

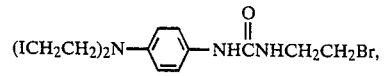

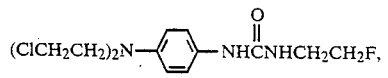

-continued

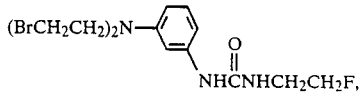

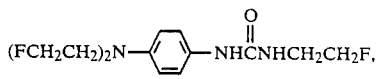

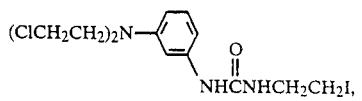

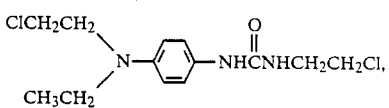

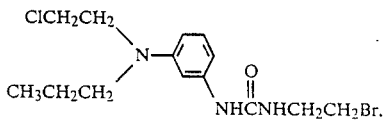

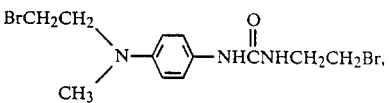

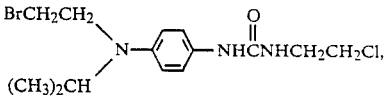

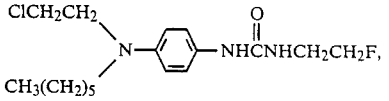

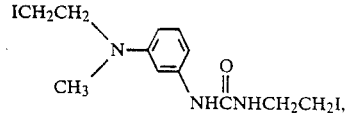

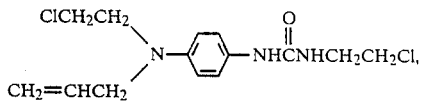

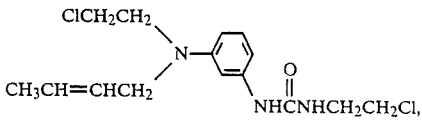

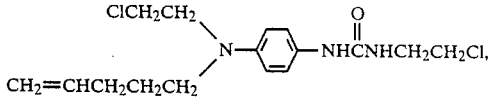

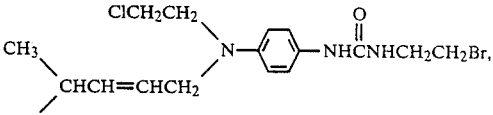

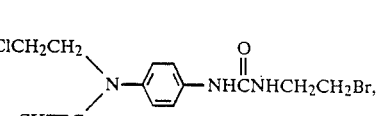

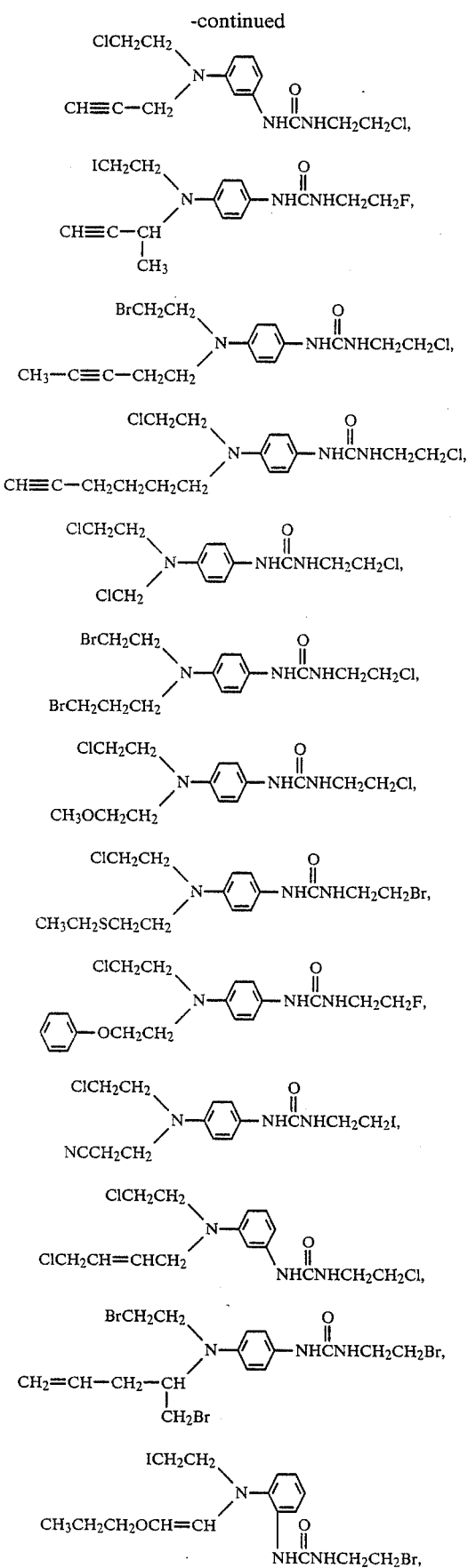
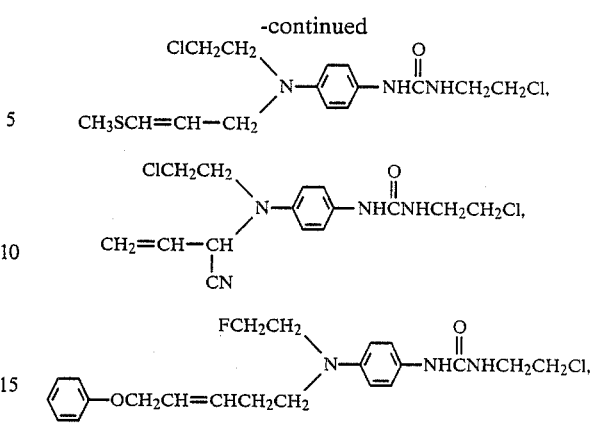

The substituted aminophenylurea derivatives of general formula (I) are usually solids which are white, pale yellow, pale yellowish brown or pale brown according to the types of the substituents $X^1$, $X^2$ and R. They are generally soluble in acetone, N,N-dimethylformamide, dimethyl sulfoxide, dimethoxyethane, methanol and ethanol, sparingly soluble in ligroin, hexane, chloroform and benzene, and in most cases, nearly insoluble in water.

The structure of the compounds of this invention, as represented by general formula (I), can be determined by the following methods.

(A) In their infrared absorption spectra, an absorption based on the NH linkage can be observed in the vicinity of 3350–3300 $cm^{-1}$, and a characteristic absorption based on the carbonyl linkage of the ureido group can be observed in the vicinity of 1650–1610 $cm^{-1}$.

(B) By measuring the mass spectrum of the compound of this invention and observing peaks specified by m/e, the molecular weight of the compound and the manner of bonding between the atoms in the molecule can be determined. Specifically, as the compound shows a molecular ion peak (to be abbreviated $M^{\oplus}$), the molecular weight of the compound can be established. It is also characteristic that a peak corresponding to $M^{\oplus}-X^1$ or $X^2$ resulting from liberation of one halogen atom ($X^1$ or $X^2$) from the molecular ion peak is observed.

(C) By measuring the $^{13}C$ nuclear magnetic resonance spectrum ($^{13}C$-NMR) of the compound, the number of carbon atoms, the manner of arrangment of carbon chains and the manner of bonding of carbon atoms in the compound can be determined. As a typical example, the chemical shifts (δ, ppm using tetramethylsilane as a standard) of peaks appearing in the $^{13}C$-NMR spectrum of a compound of this invention represented by general formula (I) in which $X^1$ and $X^2$ are Cl and R is $ClCH_2CH_2-$ can be analyzed as follows:

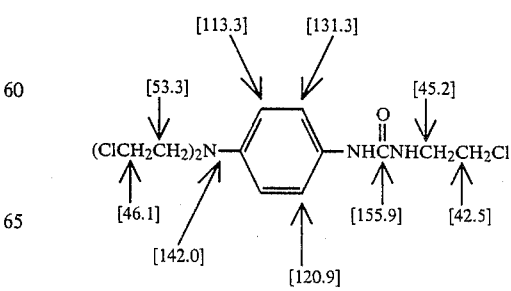

(D) The weight percents of carbon, hydrogen, nitrogen and halogen and optionally sulfur are determined by elemental analysis. Thereafter by subtracting the sum of the determined weights of these elements from 100, the weight of oxygen can be calculated. Hence, the composition formula of the compound can be determined.

The compounds of formula (I) can form acid addition salts at the substituted amino group. Examples of such acid addition salts are shown below.

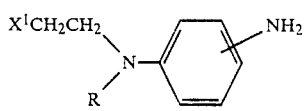
(II)

wherein $X^1$ and R are the same as defined above, or its salt with a β-haloethyl isocyanate of the general formula

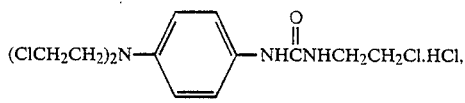

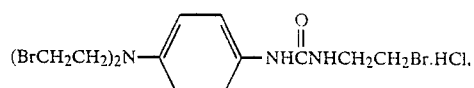

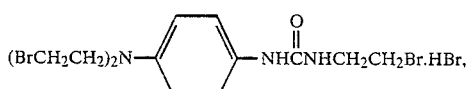

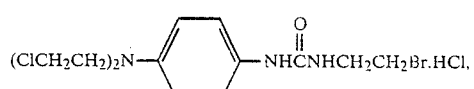

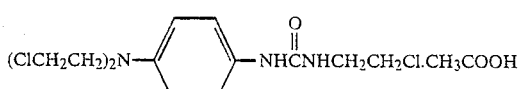

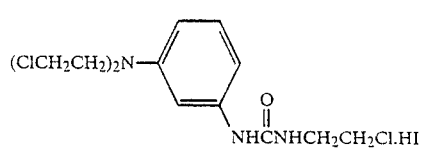

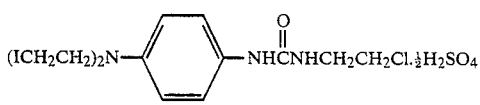

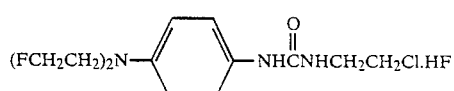

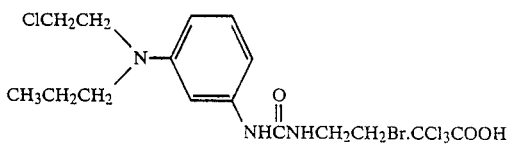

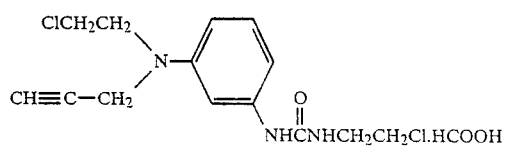

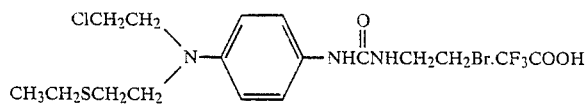

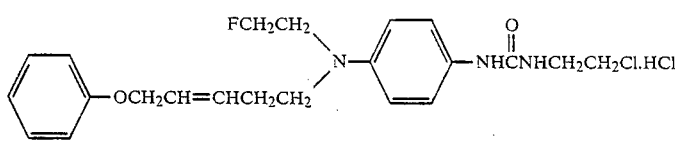

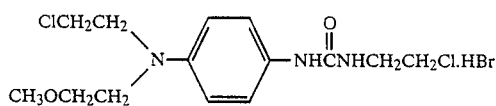

$$X^2CH_2CH_2NCO \qquad (III)$$

wherein $X^2$ is the same as defined above, or (b) reacting a substituted amino-phenyl isocyanate compound of the general formula

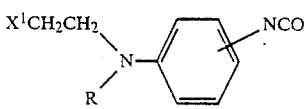
(IV)

Those acid addition salts which are pharmaceutically acceptable are preferred.

According to the present invention, the compounds of formula (I) and its acid addition salts can be produced by (a) reacting a substituted amino-aniline compound of the general formula wherein $X^1$ and R are the same as defined above, with a β-haloethylamine of the general formula

X²CH₂CH₂NH₂     (V)

wherein X² is the same as defined above, or its salt, and (c) if desired, converting the resulting compound of formula (I) into its acid addition salt.

Both the reaction of the compound of formula (II) with the compound of formula (III) and the reaction of the compound of formula (IV) with the compound of formula (V) in process variants (a) and (b) are addition reactions involving the formation of a urea linkage between the primary amino group and the isocyanate group, and can be carried out by methods known per se. For example, these reactions can be carried out in the absence of a solvent. Generally, however, the reaction is preferably carried out in a solvent. Suitable solvents used in these reactions include, for example, ethers such as ethyl ether, tetrahydrofuran, dimethoxyethane and dioxane; amides such as N,N-dimethylformamide; halogenated hydrocarbons such as dichloromethane; and hydrocarbons such as hexane. The reaction temperature is not critical, and can be varied over a broad range depending upon the types of the starting materials, etc. Generally, temperatures of about −20° C. to about 100° C., preferably 0° C. to 70° C., are advantageously employed. The reaction time varies depending upon the reaction temperature, etc. Generally, however, the reactions can be terminated within several minutes to several days.

The ratio of the reactants charged is not particularly limited. Generally, it is convenient to use 0.8 to 1.2 moles, preferably about 1 mole, of the compound of formula (III) or (V) per mole of the compound of formula (II) or (IV).

The compound of formula (I) formed by the above reactions can be separated from the reaction mixture and purified by methods known per se, for example filtration, solvent evaporation, crystallization, recrystallization, chromatography, or combinations of these. For example, when the compound of formula (I) is sparingly soluble or insoluble in the reaction solvent to form precipitates after the reaction, it can be purified by separating it from the reaction mixture by filtration, and optionally washing the filtrate and/or recrystallizing it from a suitable solvent. When the compound of formula (I) remains dissolved in the reaction solvent, it can be purified by evaporating the solvent and recrystallizing or chromatographing the residue.

The substituted amino-aniline compounds of formula (II), the β-haloethyl isocyanates of formula (III), the substituted aminophenyl isocyanate compounds of formula (IV) and the β-haloethylamines of formula (V) used as reactants in the process variants (a) and (b) are generally known per se. Even novel compounds falling within these formulae could be produced as in the production of the known compounds. The compounds of formulae (II) and (V) can be used in the form of salts. There is no particular limitation on the types of such salts. Generally, salts formed with inorganic or organic acids such as hydrochloric acid, hydrobromic acid, hydriodic acid, hydrofluoric acid, sulfuric acid, formic acid, oxalic acid, acetic acid, trichloroacetic acid and trifluoroacetic acid can be used. The hydrochlorides and hydrobromides are particularly preferred.

Usually, the number of acids to add to the β-haloethylamine of formula (V) is one, but in the case of the salt of the substituted aminoaniline of formula (II), the number of acids which add to it is in many cases two since it has two basic nitrogen atoms in the molecule.

When the compound of formula (II) or formula (V) is used in the form of a salt, the reaction may be conveniently promoted by adding a base to the reaction system. Examples of the bases are tertiary amines such as triethylamine, trimethylamine, tributylamine and pyridine, and inorganic bases such as sodium carbonate, potassium carbonate, sodium hydroxide, potassium hydroxide, lithium hydroxide and sodium hydride.

Since the compound of formula (I) produced by the process variant (a) or (b) has an amino group in the molecule, it can exist in the form of an acid addition salt. Conversion of the compound of formula (I) into its acid addition salt can be carried out by salt-forming reactions known per se. For example, the compound of formula (I) can be easily converted to a salt by treating it with an acid such as hydrochloric acid, hydrobromic acid, hydriodic acid, hydrofluoric acid, sulfuric acid, formic acid, oxalic acid, trichloroacetic acid and trifluoroacetic acid.

The substituted aminophenylurea derivatives of general formula (I) and their acid addition salts provided by this invention have excellent pharmacological properties, particularly outstanding tumor-inhibiting activity. They can be used for the treatment of various types of cancer as antitumor agents. The superior antitumor activity of the compounds of this invention can be demonstrated by the following standard antitumor activity tests on Ehrlich ascites carcinoma, Walker carcinosarcoma 256 ascites cancer, P388 leukemia, B16 melanoma, M5076 ovarian cancer and ascites hepatoma AH130 in mice or rats.

The following Test Exampoles, Preparation Examples and Formulation Examples on the substituted aminophenylurea derivatives of general formula (I) illustrate the present invention more specifically. It should be understood that the invention is in no way limited to these specific examples.

Test Example A: Ehrlich ascites carcinoma in mice

N-[p-bis(β-chloroethyl)aminophenyl]-N'-(β'-chloroethyl)urea (to be abbreviated as "CACU") was added to physiological saline (0.85%) containing a surface-active agent (Tween 80) to prepare a suspension containing a predetermined amount of CACU. Ehrlich carcinoma cells (5×10⁶) were transplanted into the peritoneal cavity of six CD2F₁-strain Swiss mice (female). For a period of 9 consecutive days starting one day after the transplantation, the suspension of CACU was intraperitoneally injected into the mice in an amount of 0.5 ml every day. From the results on the increase of lifespan over 60 days, the mean survival time (MST, days) was determined. By comparing it with the mean survival time of a control group (30 mice), T/C % was accurately calculated by a computer. Specifically, the mean survival time (days) was determined on test animals (T) and control animals (C), and T/C×100 (%) was calculated.

Physiological saline (0.85%) containing Tween 80 only was intraperitoneally injected into the mice in the control group in an amount of 0.5 ml every day for 9 consecutive days as in the treatment of the group administered with the CACU suspension. The mean survival time was 15.3 days.

The results show that at a CACU dosage of 50 mg/kg, three mice survived out of six, and T/C was more than 392%, and that at a dosage of 100 mg/kg, two mice out of six survived, the mean survival time was 45.0 days, and the T/C was 294%.

Test Example B: Walker carcinosarcoma 256 ascites tumor in rats

Walker carcinosarcoma 256 tumor cells ($1 \times 10^5$) were transplanted into the peritoneal cavity of six Sprague-Dawley rats (male), and for 5 consecutive days starting one day after the transplantation, a CACU solution prepared in the same way as in Test Example A was intraperitoneally injected into the rats, the effect on the increase of lifespan was examined over one month. It was found that at dosages of 10 mg/kg, 50 mg/kg and 25 mg/kg, all six rats survived, which meant that T/C was more than 361% in all cases. This clearly showed that the administration of CACU completely cured Walker carcinosarcoma 256.

In this test, the mean survival time in the control group was 8.3 days.

Test Example C: P388 Lymphatic leukemia in mice

P-388 lymphocytic leukemia cells ($10^6$) were transplanted into six $CDF_1$-strain mice (male). A CACU solution prepared as in Test Example A was intraperitoneally injected into the mice for 9 consecutive days starting one day after the transplantation in an amount of 0.5 ml every day. From the results on the increase of lifespan over 30 days, the mean survival time (MST, days) was determined. By comparing it with the mean survival time of a control group (30 mice), T/C % was calculated as in Test Example A. It was found that at a dosage of 50 mg/kg, T/C was 189%, and at a dosage of 25 mg/kg, T/C was 167%. Thus, it was confirmed that CACU is effective against P388 leukemia.

Test Example D: B16 Melanoma in mice

B16 Melanoma cells ($1 \times 10^6$) were transplanted into the peritoneal cavity of ten $BDF_1$-strain mice (female). A CACU solution prepared as in Test Example A was intraperitoneally injected into the mice for 9 consecutive days starting one day after the transplantation in an amount of 0.5 ml every day. From the results on the increase of lifespan over 60 days, T/C % was calculated. It was found that at a dosage of 100 mg/kg, T/C was 177%, and at a dosage of 50 mg/kg, T/C was 171%. Thus, it was confirmed that CACU is effective against B16 melanoma.

Test Example E: M5076 ovarian cancer in mice

M5076 Ovarian tumor cells ($1 \times 10^6$) were transplanted into the peritoneal cavity of $BDF_1$-strain mice (female). A CACU solution prepared as in Test Example A was intraperitoneally injected into the mice five times at intervals of 4 days starting one day from the transplantation (1st day, 5th day, 9th day, 13th day and 17th day) in an amount of 0.5 ml per day. From the results on the increase of lifespan over 60 days, T/C % was calculated. It was found that at a dosage of 200 mg/kg, five mice survived out of ten and T/C was more than 214%, and at a dosage of 100 mg/kg, seven mice survived out of ten, and T/C was more than 214%. The above results led to the confirmation that CACU is effective against M5076 ovarian tumor.

Test Example F

Various antitumor activity tests were carried out as in Test Examples A to E using the compounds of this invention produced in Examples 4 and 7 given below. The results are summarized in Table 1 below. In the table, E stands for Ehrlich carcinoma; W, Walker carcinosarcoma 256; and P, P388 leukemia.

TABLE 1

| Compound | Type of tumor | Dosage [mg/Kg] | T/C (%) |
|---|---|---|---|
| 1 | E | 50 | >392 |
|   | W | 100 | >361 |
|   | P | 50 | 167 |
|   |   | 6 | 213 |
| 2 | E | 50 | >392 |
|   | P | 50 | 218 |
|   |   | 25 | 158 |
| 3 | E | 50 | 294 |
|   | P | 50 | 186 |
|   |   | 3 | 196 |
| 4 | W | 100 | >361 |
|   | P | 50 | 151 |
|   |   | 12.5 | 167 |
| 5 | W | 75 | >361 |
|   | P | 50 | 142 |
|   |   | 25 | 195 |
| 6 | E | 25 | 294 |
|   | P | 25 | 135 |
| 7 | E | 25 | 229 |
| 8 | P | 25 | 134 |
| 9 | W | 50 | 205 |
| 10 | E | 100 | 222 |
| 11 | E | 100 | 203 |
| 12 | W | 50 | 329 |
| 13 | P | 100 | 134 |
| 14 | E | 50 | 275 |
| 15 | W | 150 | 220 |
| 16 | E | 150 | 235 |
| 17 | E | 100 | 294 |
| 18 | P | 25 | 154 |
| 19 | W | 50 | 329 |
| 20 | E | 50 | 281 |
| 21 | W | 100 | 207 |
| 22 | W | 50 | 256 |
| 23 | P | 50 | 156 |
| 24 | E | 150 | 234 |
| 25 | E | 100 | 178 |
| 26 | W | 200 | 216 |
| 27 | E | 50 | 246 |
| 28 | W | 25 | 182 |
| 29 | P | 25 | 187 |
| 30 | E | 200 | 205 |
| 31 | E | 150 | 184 |
| 32 | P | 50 | 150 |
| 33 | W | 200 | 169 |
| 34 | E | 150 | 199 |
| 35 | E | 150 | 191 |
| 36 | E | 100 | 186 |

Test Example G: Ascites hepatoma AH130 in rats

CACU obtained in Example 1 below was added to physiological saline (0.85%, 10 ml) containing a surfactant, Tween 80, (50 mg) and sodium carboxymethyl cellulose (50 mg) to prepare a suspension containing a predetermined amount of CACU. Rat ascites hepatoma AH130 cells ($10^7$; see NCI monograph No. 16) were transplanted into six Donryu rats (male) intravenously through the tail vein. Three days later, the above suspension was injected into the rats through the tail vein in a predetermined amount, and the effect on the increase of lifespan was tested over 60 days. When the CACU was administered in a dose of 25 mg/kg seven times (on the 3rd, 5th, 7th, 11th, 15th, 20th and 24th days), four rats out of six survived. On the other hand, the means survival time in a control group was 17.0 days, and at a dosage of 25 mg/kg, T/C was more than 353%.

The foregoing results clearly demonstrate that CACU shows marked antitumor activity against rat ascites hepatoma by iv/iv administration.

Test Example H: Acute toxicity in mice

A CACU solution prepared as in Test Example A was injected intraperitoneally into $CD2F_1$-strain mice (male) having a body weight of about 20 g in an amount of 2512, 1995, 1585, 1259, 1000 and 994 mg/kg, and the acute toxicity test was carried out for 20 days. The acute toxicity value (LD$_{50}$) was determined by the method of Litchfield and Wilcoxon, and found to be 1025 mg/kg.

As is clearly seen from the results of the above test examples, the substituted aminophenylurea derivatives provided by this invention have an excellent inhibitory action on various types of tumor cells with low toxicity, and are useful as medicaments for the treatment of various types of cancer.

When the compound of this invention is used as an antitumor agent, it can be administered to patients through oral, parenteral (e.g., intravenous, intramuscular, subcutaneous, intraperitoneal, intrarectal, etc.) or topical routes. The effective dosage of the compound of this invention varies deending upon the age, body weight and symptom of a patient to which it is administered, and the type of cancer. Generally, it is 800 to 0.002 mg/kg of body weight/day, preferably 500 to 0.01 mg/kg of body weight/day. The dosage prescribed for one day may be administered only once or portionwise several times (3 to 5 times) a day. The above dosage is a mere guideline, and depending upon the judgment of a physician who treat the patient, the anti-tumor compound may be administered in dosages outside the above range.

In administration, the compound of this invention may be formulated into pharmaceutical preparations in various forms suitable for the desired route of administration (oral, parenteral, topical) by mixing it with pharmaceutically acceptable adjuvants such as vehicles, fillers, diluents, excipients, binders, disintegrants, corrigents, emulsifiers, etc. For example, for oral administration, the compound may be formulated into tablets, powders, granules, syrups, capsules, etc. For parenteral administration, the compound may be formulated into solutions, suspensions, emulsions, suppositories, etc. For topical administration, the compound may be formulated into ointments, hard ointments, creams, etc.

Suitable adjuvants used in pharmaceutical formulation include, for example, water, gelatin, gum arabic, lactose, sucrose, glucose, starch, magnesium stearate, talc, vegetable oils, polyalkylene glycols, white petrolatum, glycerol, sodium stearate, carboxymethyl cellulose, alcohols, and esters.

The concentration of the compound of this invention in such drug formulations is not particularly limited, and may be varied widely according to the form of the drug formulation. Generally, it is in the range of 0.05 to 90% by weight, preferably 1 to 60% by weight.

PREPARATION EXAMPLE 1

A mixture of p-bis($\beta$-chloroethyl)aminoaniline.2HCl (4.05 g; 0.013 mole), hexane (80 ml) and triethylamine (2.15 g; 0.021 mole) was cooled with dry ice, and $\beta$-chloroethyl isocyanate (2.03 g; 0.019 mole) was added with stirring. Two hours later, the temperature of the reaction mixture was returned to room temperature, and it was further stirred for 2 days. Then, the mixture was heated under reflux for 2 hours. Water (150 ml) was added to the reaction mixture. The insoluble material was filtered, washed with water, and dried to give a white solid (5.17 g). Recrystallization of the white solid from acetonitrile gave white crystals (2.73 g; melting point 131°–133° C.). The infrared absorption spectrum of this product is shown in FIG. 1. It showed a strong absorption based on the NH linkage at 3300 cm$^{-1}$ and a strong absorption based on the carbonyl linkage of the ureido group at 1630 cm$^{-1}$. The elemental analysis values were: C 45.83%, H 5.25%, N 12.49%, which well agreed with the calculated values for the composition formula $C_{13}H_{18}N_3OCl_3$ (338.66) which were C 46.10%, H 5.36%, N 12.41%. Its mass spectrum showed molecular ion peaks (M⊕) corresponding to the molecular weight at m/e=339 and 337, peaks corresponding to the liberation of a chlorine atom from the molecular ion peaks [M⊕-Cl] at m/e=303 and 301, and strong peaks corresponding to the fragment [M⊕-HCl-CH$_2$Cl] at m/e=254 and 252. The $^{13}$C-NMR of the compound was measured in dimethyl sulfoxide using tetramethylsilane as a standard to show the chemical shifts ($\delta$, ppm) as follows.

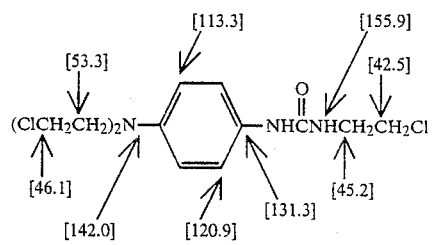

All the above results determined the resulting white solid to be N-[p-bis($\beta$-chloroethyl)aminophenyl]-N'-($\beta'$-chloroethyl)urea. After recrystallization, the yield of the product was 61.1%.

PREPARATION EXAMPLE 2

Triethylamine (21.27 g) was added to a mixture of p-bis($\beta$-chloroethyl)aminoaniline.2HCl (17.20 g; 0.051 mole) and ether (400 ml), and the mixture was stirred for 5 hours. The precipitate was removed by filtration, and to the ether solution of p-bis($\beta$-chloroethyl)aminoaniline obtained as a filtrate was added gradually $\beta$-chloroethyl isocyanate (9.68 g). The mixture was stirred at room temperature for 1 day. The resulting precipitate was collected by filtration to give N-[p-bis($\beta$-chloroethyl)aminophenyl]-N'-($\beta'$-chloroethyl)urea (16.26 g) as white crystals which was the same as the product of Example 1. The yield was 94.1%.

PREPARATION EXAMPLE 3

A mixture of $\beta$-chloroethylamine.HCl (5.80 g, 0.05 mole), hexane (60 ml), N,N-dimethylformamide (30 ml) and tributylamine (14.83 g; 0.08 mole) was cooled to −10° C., and an ether solution (100 ml) of p-bis($\beta$-chloroethyl)aminophenyl isocyanate (12.9 g; 0.05 mole) was added with stirring. One hour later, the reaction mixture was heated at 34° C. for 6 hours. Low-boiling fractions were removed by distillation under reduced pressure. The residue was poured into ice water (500 ml), and the resulting white solid was collected by filtration and dried to give N-[p-bis($\beta$-chloroethyl)aminophenyl]-N'-($\beta'$-chloroethyl)urea (14.61 g). The yield was 86.3%.

Figure 2:
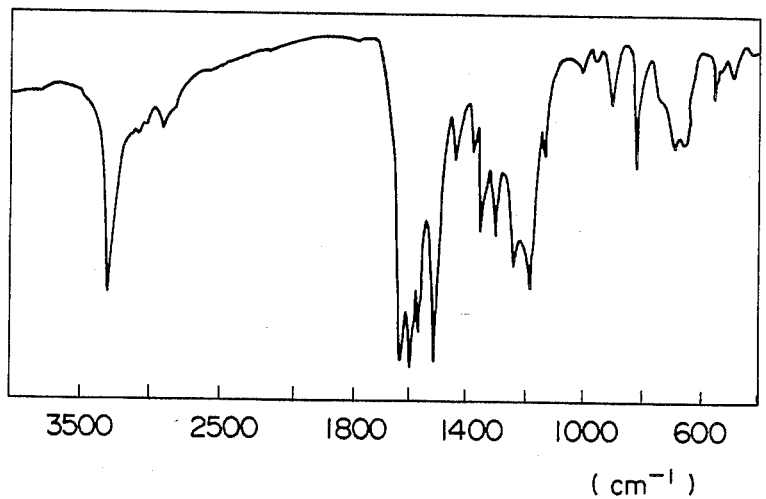

PREPARATION EXAMPLE 4 p-Bis($\beta$-bromoethyl)aminoaniline.2HCl (2.93 g) was reacted with triethylamine (2.90 g) in ether (150 ml). The reaction mixture was filtered, and $\beta$-bromoethyl isocyanate (1.23 g) was added to the filtrate to give a white solid (3.32 g; melting point 103°–105° C.). The infrared absorption spectrum of the solid was as shown in FIG. 2. It was very similar to the infrared absorption spectrum of N-[p-bis($\beta$-chloroethyl)aminophenyl]-N'-($\beta'$-chloroethyl)urea obtained in Example 1, and showed a strong absorption based on the NH linkage at 3300 cm$^{-1}$ and a strong absorption based on the carbonyl linkage of the ureido group at 1625 cm$^{-1}$. The elemental analysis values were C 33.44%, H 3.47%, and N 8.84% which agreed with the calculated values for the composition formula $C_{13}H_{18}N_3OBr_3$ (472.04) which were C 33.908%, H 3.84%, N 8.90%. Its mass spectrum showed M$^\oplus$ at m/e=472 and peaks corresponding to [M$^\oplus$-Br] at m/e=393 and 392. The foregoing results clearly show that the resulting white solid is N-[p-bis($\beta$-bromoethyl)aminophenyl]-N'-($\beta'$-bromoethyl)urea (designated as compound No. 1). The yield was 95.0%.

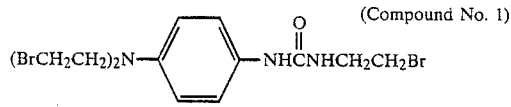

(Compound No. 1)

PREPARATION EXAMPLE 5 p-bis($\beta$-Bromoethyl)aminoaniline.2HBr (6.73 g), sodium carbonate (4.42 g) and $\beta$-bromoethyl isocyanate (2.09 g) were added to dimethoxyethane (200 ml). The mixture was stirred at room temperature for 3 days. The resulting solid was removed by filtration. The filtrate was concentrated under reduced pressure, and ice water (200 ml) was added. The resulting white solid was collected by filtration, and dried to give N-[p-bis($\beta$-bromoethyl)aminophenyl]-N'-($\beta'$-bromoethyl)urea (5.35 g) which was the same as the product obtained in Example 4. The yield waas 81.5%.

PREPARATION EXAMPLE 6

While the ether solution (200 ml) of N-[p-bis($\beta$-chloroethyl)aminophenyl]-N'-($\beta'$-chloroethyl)urea (3.39 g) obtained in Example 1 was cooled in an ice bath, dry hydrogen chloride gas was blown into it over 2 hours. Subsequent filtration gave a pale brown solid (3.73 g).

The elementary analysis values of this product were C 41.34%, H 5.25%, N 11.08%, Cl 37.90% which well agreed with the calculated values (C 41.62%, H 5.10%, N 11.20% and Cl 37.81%) for the composition formula $C_{13}H_{19}N_3OCl_4$ (375.13).

When the above product was added to water, a white solid remained as an insoluble material, and the aqueous solution was acidic. This white solid was determined to be N-[p-bis($\beta$-chloroethyl)aminophenyl]-N'-($\beta'$-chloroethyl)urea.

It was clear from the foregoing results that the pale brown solid obtained in ether was N-[p-bis($\beta$-chloroethyl)aminophenyl]-N'-($\beta'$-chloroethyl)urea hydrochloride.

PREPARATION EXAMPLE 7

The substituted aminophenylurea derivatives shown in Table 2 were synthesized by the same methods as described in Examples 1 to 5. Table 2 also gives the appearances of the urea derivatives, the characteristic absorptions in the infrared absorption spectra, the results of mass analysis and elemental analysis, and the yields of the compounds obtained.

TABLE 2

| Compound No. | Structural formula and properties | IR(cm$^{-1}$) and MS (M$^⊕$) characteristics | Composition formula (molecular weight) [Yield] | Elemental analysis (%) (calculated values are parenthesized) | | |
|---|---|---|---|---|---|---|
| | | | | C | H | N |
| 2 | (ClCH$_2$CH$_2$)$_2$N—⟨benzene⟩—NHCNHCH$_2$CH$_2$Br (C=O)<br>White solid, mp. 110–113° C. | 3310 (NH)<br>1630 (C=O)<br>m/e 383 | C$_{13}$H$_{18}$N$_3$OCl$_2$Br<br>(383.12)<br>[80.3%] | 40.94 (40.75) | 4.09 (4.73) | 10.76 (10.97) |
| 3 | (BrCH$_2$CH$_2$)$_2$N—⟨benzene⟩—NHCNHCH$_2$CH$_2$Cl (C=O)<br>White solid, mp. 126–127° C. | 3300 (NH)<br>1630 (C=O)<br>m/e 427 | C$_{13}$H$_{18}$N$_3$OClBr$_2$<br>(427.58)<br>[98.9%] | 36.88 (36.51) | 3.62 (4.24) | 9.80 (9.83) |
| 4 | (ICH$_2$CH$_2$)$_2$N—⟨benzene⟩—NHCNHCH$_2$CH$_2$Cl (C=O)<br>White solid, mp. 133–135° C. | 3320 (NH)<br>1635 (C=O)<br>m/e 521 | C$_{13}$H$_{18}$N$_3$OClI$_2$<br>(521.57)<br>[66.3%] | 30.10 (29.93) | 3.24 (3.48) | 7.85 (8.06) |
| 5 | (ICH$_2$CH$_2$)$_2$N—⟨benzene⟩—NHCNHCH$_2$CH$_2$Br (C=O)<br>White solid, mp. 146–148° C. | 3300 (NH)<br>1630 (C=O)<br>m/e 567 | C$_{13}$H$_{18}$N$_3$OBrI$_2$<br>(566.03)<br>[36.2%] | 27.14 (27.58) | 2.86 (3.20) | 7.14 (7.42) |
| 6 | (ClCH$_2$CH$_2$)$_2$N—⟨benzene⟩—NHCNHCH$_2$CH$_2$F (C=O)<br>White solid | 3330 (NH)<br>1640 (C=O)<br>m/e 322 | C$_{13}$H$_{18}$N$_3$OCl$_2$F<br>(322.21)<br>[82.4%] | 48.90 (48.46) | 5.44 (5.63) | 13.26 (13.04) |
| 7 | (BrCH$_2$CH$_2$)$_2$N—⟨benzene, meta⟩—NHCNHCH$_2$CH$_2$F (C=O)<br>White solid | 3330 (NH)<br>1640 (C=O)<br>m/e 411 | C$_{13}$H$_{18}$N$_3$OBr$_2$F<br>(411.11)<br>[78.5%] | 38.23 (37.98) | 4.28 (4.41) | 10.56 (10.22) |
| 8 | (FCH$_2$CH$_2$)$_2$N—⟨benzene⟩—NHCNHCH$_2$CH$_2$F (C=O)<br>White solid | 3335 (NH)<br>1645 (C=O)<br>m/e 289 | C$_{13}$H$_{18}$N$_3$OF$_3$<br>(289.30)<br>[54.6%] | 54.16 (53.97) | 6.00 (6.27) | 14.31 (14.52) |

TABLE 2-continued

| Compound No. | Structural formula and properties | IR(cm$^{-1}$) and MS (M$^{\oplus}$) characteristics | Composition formula (molecular weight) [Yield] | Elemental analysis (%) (calculated values are parenthesized) | | |
|---|---|---|---|---|---|---|
| | | | | C | H | N |
| 9 | (ClCH$_2$CH$_2$)$_2$N—C$_6$H$_4$—NHCNHCH$_2$CH$_2$I (meta), C=O<br>White solid | 3310 (NH)<br>1630 (C=O)<br>m/e 430 | C$_{13}$H$_{18}$N$_3$OCl$_2$I<br>(430.12)<br>[88.7%] | 36.55<br>(36.30) | 4.53<br>(4.22) | 10.02<br>(9.77) |
| 10 | ClCH$_2$CH$_2$, CH$_3$CH$_2$ — N—C$_6$H$_4$—NHCNHCH$_2$CH$_2$Cl (para), C=O<br>White solid | 3315 (NH)<br>1630 (C=O)<br>m/e 304 | C$_{13}$H$_{19}$N$_3$OCl$_2$<br>(304.22)<br>[57.0%] | 51.72<br>(51.33) | 5.97<br>(6.29) | 13.76<br>(13.81) |
| 11 | ClCH$_2$CH$_2$, CH$_3$CH$_2$CH$_2$ — N—C$_6$H$_4$—NHCNHCH$_2$CH$_2$Br (meta), C=O<br>White solid | 3310 (NH)<br>1630 (C=O)<br>m/e 363 | C$_{14}$H$_{21}$N$_3$OBrCl<br>(362.70)<br>[46.9%] | 46.53<br>(46.36) | 5.82<br>(5.84) | 11.37<br>(11.59) |
| 12 | BrCH$_2$CH$_2$, CH$_3$ — N—C$_6$H$_4$—NHCNHCH$_2$CH$_2$Br (para), C=O<br>White solid | 3310 (NH)<br>1630 (C=O)<br>m/e 379 | C$_{12}$H$_{17}$N$_3$OBr$_2$<br>(379.09)<br>[93.4%] | 37.81<br>(38.02) | 4.53<br>(4.52) | 11.29<br>(11.08) |
| 13 | BrCH$_2$CH$_2$, (CH$_3$)$_2$CH — N—C$_6$H$_4$—NHCNHCH$_2$CH$_2$Cl (para), C=O<br>White solid | 3300 (NH)<br>1630 (C=O)<br>m/e 363 | C$_{14}$H$_{21}$N$_3$OBrCl<br>(362.70)<br>[86.1%] | 46.04<br>(46.36) | 6.11<br>(5.84) | 11.38<br>(11.59) |
| 14 | ClCH$_2$CH$_2$, CH$_3$(CH$_2$)$_5$ — N—C$_6$H$_4$—NHCNHCH$_2$CH$_2$F (para), C=O<br>White solid | 3325 (NH)<br>1640 (C=O)<br>m/e 344 | C$_{17}$H$_{27}$N$_3$OClF<br>(343.87)<br>[49.4%] | 59.29<br>(59.38) | 8.14<br>(7.91) | 12.59<br>(12.22) |

TABLE 2-continued

| Compound No. | Structural formula and properties | IR(cm$^{-1}$) and MS (M$^\oplus$) characteristics | Composition formula (molecular weight) [Yield] | Elemental analysis (%) (calculated values are parenthesized) | | |
|---|---|---|---|---|---|---|
| | | | | C | H | N |
| 15 | ICH$_2$CH$_2$–N(CH$_3$)–C$_6$H$_4$–NHCNHCH$_2$CH$_2$I (meta), C=O<br>White solid | 3320 (NH)<br>1635 (C=O)<br>m/e 473 | C$_{12}$H$_{17}$N$_3$OI$_2$<br>(473.10)<br>[74.8%] | 30.40<br>(30.47) | 3.33<br>(3.62) | 8.85<br>(8.88) |
| 16 | ClCH$_2$CH$_2$, CH$_2$=CHCH$_2$–N–C$_6$H$_4$–NHCNHCH$_2$CH$_2$Cl<br>White solid | 3325 (NH)<br>1635 (C=O)<br>m/e 316 | C$_{14}$H$_{19}$N$_3$OCl$_2$<br>(316.23)<br>[58.2%] | 52.94<br>(53.17) | 5.81<br>(6.06) | 13.30<br>(13.29) |
| 17 | ClCH$_2$CH$_2$, CH≡C–N–C$_6$H$_4$–NHCNHCH$_2$CH$_2$Br<br>White solid | 3315 (NH)<br>1630 (C=O)<br>m/e 345 | C$_{13}$H$_{15}$N$_3$OBrCl<br>(344.64)<br>[36.9%] | 45.25<br>(45.31) | 4.03<br>(4.39) | 12.47<br>(12.19) |
| 18 | ClCH$_2$CH$_2$, ClCH$_2$–N–C$_6$H$_4$–NHCNHCH$_2$CH$_2$Cl<br>Pale brown solid | 3320 (NH)<br>1630 (C=O)<br>m/e 325 | C$_{12}$H$_{16}$N$_3$OCl$_3$<br>(324.64)<br>[81.0%] | 44.52<br>(44.40) | 5.21<br>(4.97) | 13.26<br>(12.94) |
| 19 | BrCH$_2$CH$_2$, BrCH$_2$CH$_2$CH$_2$–N–C$_6$H$_4$–NHCNHCH$_2$CH$_2$Cl<br>White solid | 3310 (NH)<br>1630 (C=O)<br>m/e 442 | C$_{14}$H$_{20}$N$_3$OClBr$_2$<br>(441.59)<br>[75.5%] | 37.84<br>(38.08) | 4.53<br>(4.56) | 9.46<br>(9.52) |
| 20 | ClCH$_2$CH$_2$, CH$_3$OCH$_2$CH$_2$–N–C$_6$H$_4$–NHCNHCH$_2$CH$_2$Cl<br>White solid | 3300 (NH)<br>1630 (C=O)<br>m/e 334 | C$_{14}$H$_{21}$N$_3$O$_2$Cl$_2$<br>(334.25)<br>[78.2%] | 50.39<br>(50.31) | 6.02<br>(6.33) | 12.40<br>(12.57) |
| 21 | ClCH$_2$CH$_2$, CH$_3$CH$_2$SCH$_2$CH$_2$–N–C$_6$H$_4$–NHCNHCH$_2$CH$_2$Br | 3310 (NH)<br>1630 (C=O)<br>m/e 409 | C$_{15}$H$_{23}$N$_3$OSClBr<br>(408.78)<br>[49.7%] | 44.23<br>(44.07) | 5.67<br>(5.67) | 10.11<br>(10.28) |

TABLE 2-continued

| Compound No. | Structural formula and properties | IR(cm$^{-1}$) and MS (M⊕) characteristics | Composition formula (molecular weight) [Yield] | Elemental analysis (%) (calculated values are parenthesized) | | |
|---|---|---|---|---|---|---|
| | | | | C | H | N |
| 22 | Pale yellow solid 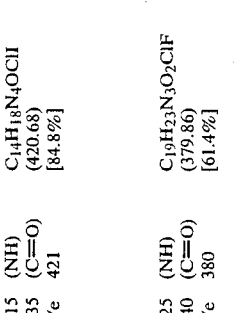 | 3315 (NH) 1635 (C=O) m/e 421 | $C_{14}H_{18}N_4OClI$ (420.68) [84.8%] | 40.15 (39.97) | 4.27 (4.31) | 13.68 (13.32) |
| 23 | Pale yellow solid 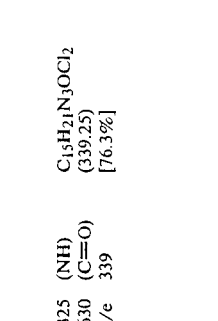 | 3325 (NH) 1640 (C=O) m/e 380 | $C_{19}H_{23}N_3O_2ClF$ (379.86) [61.4%] | 60.24 (60.08) | 6.36 (6.10) | 11.40 (11.06) |
| 24 | White solid 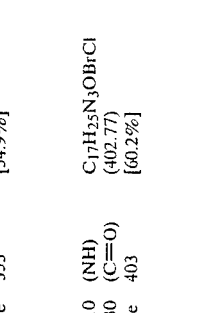 | 3325 (NH) 1630 (C=O) m/e 339 | $C_{15}H_{21}N_3OCl_2$ (339.25) [76.3%] | 52.84 (53.10) | 6.42 (6.24) | 12.50 (12.39) |
| 25 | 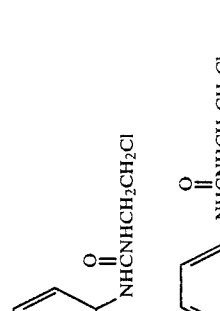 | 3325 (NH) 1630 (C=O) m/e 353 | $C_{16}H_{23}N_3OCl_2$ (353.27) [54.9%] | 54.39 (54.39) | 6.30 (6.56) | 12.11 (11.89) |
| 26 | 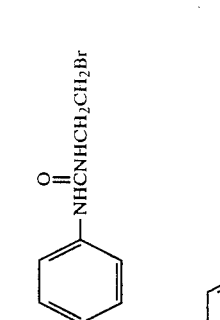 | 3310 (NH) 1630 (C=O) m/e 403 | $C_{17}H_{25}N_3OBrCl$ (402.77) [60.2%] | 50.72 (50.69) | 5.88 (6.26) | 10.27 (10.43) |
| 27 |  | 3325 (NH) 1635 (C=O) m/e 365 | $C_{15}H_{20}N_3OCl_3$ (364.70) [45.8%] | 49.42 (49.40) | 5.69 (5.53) | 11.40 (11.52) |

TABLE 2-continued

| Compound No. | Structural formula and properties | IR(cm$^{-1}$) and MS (M$^{\oplus}$) characteristics | Composition formula (molecular weight) [Yield] | Elemental analysis (%) (calculated values are parenthesized) | | |
|---|---|---|---|---|---|---|
| | | | | C | H | N |
| 28 | 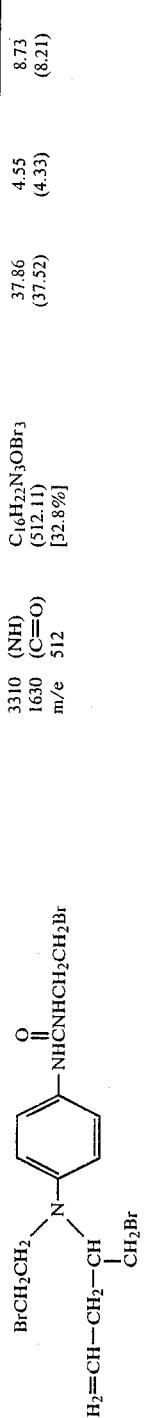 | 3310 (NH) 1630 (C=O) m/e 512 | C$_{16}$H$_{22}$N$_3$OBr$_3$ (512.11) [32.8%] | 37.86 (37.52) | 4.55 (4.33) | 8.73 (8.21) |
| 29 | 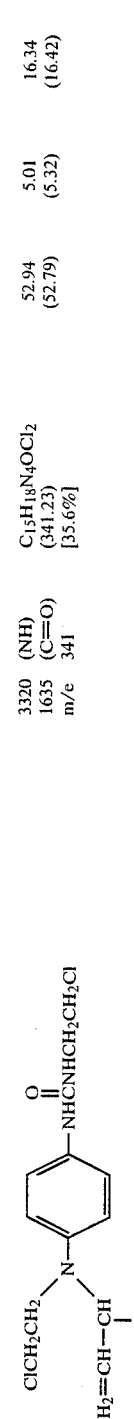 | 3320 (NH) 1635 (C=O) m/e 341 | C$_{15}$H$_{18}$N$_4$OCl$_2$ (341.23) [35.6%] | 52.94 (52.79) | 5.01 (5.32) | 16.34 (16.42) |
| 30 | 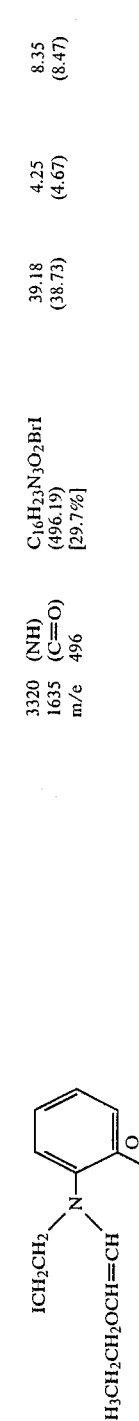 | 3320 (NH) 1635 (C=O) m/e 496 | C$_{16}$H$_{23}$N$_3$O$_2$BrI (496.19) [29.7%] | 39.18 (38.73) | 4.25 (4.67) | 8.35 (8.47) |
| 31 | 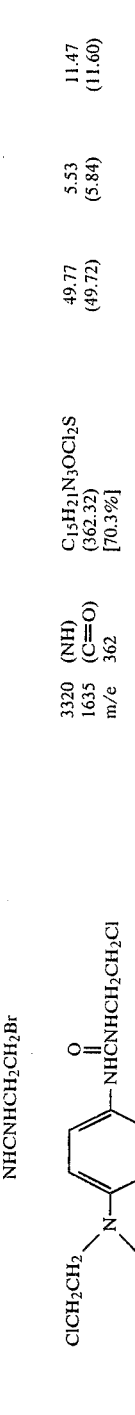 | 3320 (NH) 1635 (C=O) m/e 362 | C$_{15}$H$_{21}$N$_3$OCl$_2$S (362.32) [70.3%] | 49.77 (49.72) | 5.53 (5.84) | 11.47 (11.60) |
| 32 | 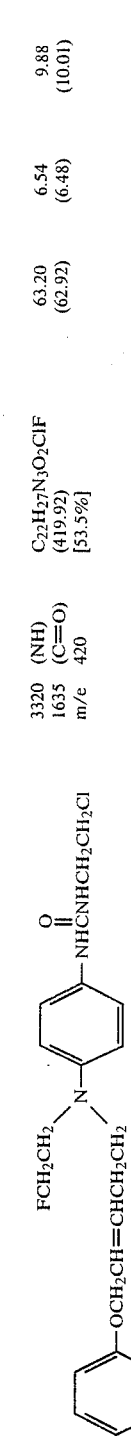 | 3320 (NH) 1635 (C=O) m/e 420 | C$_{22}$H$_{27}$N$_3$O$_2$ClF (419.92) [53.5%] | 63.20 (62.92) | 6.54 (6.48) | 9.88 (10.01) |
| 33 | 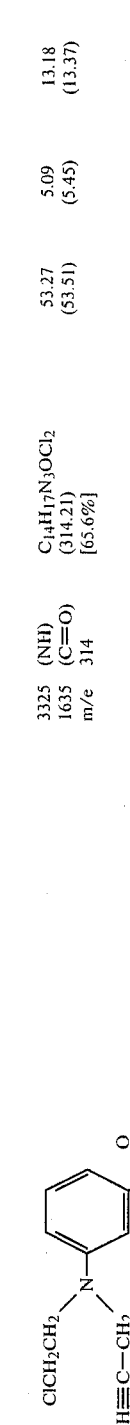 | 3325 (NH) 1635 (C=O) m/e 314 | C$_{14}$H$_{17}$N$_3$OCl$_2$ (314.21) [65.6%] | 53.27 (53.51) | 5.09 (5.45) | 13.18 (13.37) |

TABLE 2-continued
| Compound No. | Structural formula and properties | IR(cm$^{-1}$) and MS (M⊕) characteristics | Composition formula (molecular weight) [Yield] | Elemental analysis (%) (calculated values are parenthesized) | | |
|---|---|---|---|---|---|---|
| | | | | C | H | N |
| 34 |  | 3335 (NH) 1645 (C=O) m/e 403 | C$_{15}$H$_{19}$N$_3$OFI (403.23) [33.3%] | 44.84 (44.68) | 4.66 (4.75) | 10.59 (10.42) |
| 35 |  | 3325 (NH) 1635 (C=O) m/e 386 | C$_{16}$H$_{21}$N$_3$OBrCl (386.73) [48.0%] | 49.30 (49.69) | 5.46 (5.47) | 10.75 (10.87) |
| 36 |  | 3325 (NH) 1630 (C=O) m/e 356 | C$_{17}$H$_{23}$N$_3$OCl$_2$ (356.28) [71.4%] | 57.49 (57.31) | 6.22 (6.51) | 12.03 (11.79) |

Typical examples of the drug formulations in accordance with this invention will now be given.

FORMULATION EXAMPLE 1

Injectable preparation for intravenous administration:

Five parts of sodium carboxymethyl cellulose, 5 parts of a surfactant and 20 parts of the compound of this invention were well mixed with stirring. Fifty parts of physiological saline (0.85%) was added to the mixture, and the mixture was further stirred to prepare an injectable preparation.

FORMULATION EXAMPLE 2

Injectable preparation for intramuscular administration:

Two parts of benzyl alcohol, 60 parts of propylene glycol and 10 parts of the compound of the invention were added to 20 parts of distilled water. They were mixed to form an injectable preparation.

FORMULATION EXAMPLE 3

Suppository:

Sodium stearate (9 parts) was added to 90 parts of glycerol heated to 120° C. on an oil bath. Five parts of purified water was added to the mixture and thoroughly mixed. Then, 2 parts of the compound of this invention was added and the mixture stirred vigorously. The hot solution was immediately injected into a metallic suppository form, and allowed to cool to produce a suppository.

FORMULATION EXAMPLE 4

Tablets:

One hundred parts of the compound of this invention was added to a mixture of 3000 parts of lactose, 40 part of tartaric acid and 57 parts of stearic acid with stirring. After 100 parts of 5% starch paste was added as a binder, granules was formulated by the wet method. Tablets were manufactured from the granules by a tableting machine.

What is claimed is:

1. A substituted aminophenylurea derivative represented by the formula

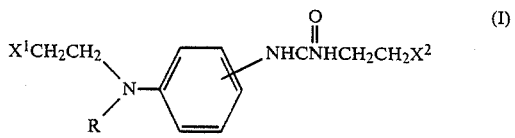

wherein $X^1$ and $X^2$ are identical or different and each represents a halogen atom, and
R is selected from the group consisting of $C_1$-$C_6$ alkyl, halo $C_1$-$C_6$ alkyl, $C_1$-$C_6$ alkoxy $C_1$-$C_6$ alkyl, $C_1$-$C_6$ alkylthio $C_1$-$C_6$ alkyl, phenoxy($C_1$-$C_6$ alkyl), cyano($C_1$-$C_6$ alkyl), $C_2$-$C_6$ alkenyl, halo($C_2$-$C_6$ alkenyl), $C_1$-$C_6$ alkoxy $C_2$-$C_6$ alkenyl, $C_1$-$C_6$ alkylthio $C_2$-$C_6$ alkenyl, phenoxy $C_2$-$C_6$ alkenyl, cyano($C_2$-$C_6$ alkenyl) and $C_2$-$C_6$ alkynyl, or an acid addition salt thereof.

2. The substituted aminophenylurea derivative of claim 1 wherein R is halo($C_1$-$C_6$ alkyl).

3. The substituted aminophenylurea derivative of claim 1 wherein R is halo($C_1$-$C_4$ alkyl).

4. The substituted aminophenylurea derivative of claim 1 which is a bis(haloethyl)aminophenylurea derivative represented by the following formula

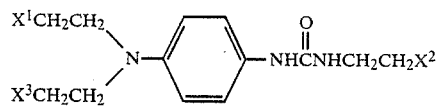

wherein $X^1$, $X^2$ and $X^3$ are identical or different and each represents a halogen atom,
or its acid addition salt.

5. The substituted aminophenylurea derivative of claim 4 wherein each of $X^1$, $X^2$ and $X^3$ are chlorine atoms.

6. The substituted aminophenylurea derivative of claim 1 wherein R is $C_1$-$C_4$ alkyl.

7. The substituted aminophenylurea derivative of claim 1 wherein R is $C_1$-$C_4$ alkoxy $C_1$-$C_4$ alkyl.

8. The substituted aminophenylurea derivative of claim 1 wherein R is $C_1$-$C_4$ alkylthio $C_1$-$C_4$ alkyl.

9. The substituted aminophenylurea derivative of claim 1 wherein the alkoxy and alkylthio each contain up to 4 carbon atoms.

10. The substituted aminophenylurea derivative of claim 1 wherein R is phenoxy($C_1$-$C_4$ alkyl).

11. The substituted aminophenylurea derivative of claim 1 wherein R is cyano($C_1$-$C_4$ alkyl).

12. The substituted aminophenylurea derivative of claim 1 wherein R is $C_2$-$C_4$ alkenyl.

13. The substituted aminophenylurea derivative of claim 1 wherein R is halo $C_2$-$C_4$ alkenyl.

14. The substituted aminophenylurea derivative of claim 1 wherein R is $C_1$-$C_4$ alkoxy $C_2$-$C_4$ alkenyl.

15. The substituted aminophenylurea derivative of claim 1 wherein R is $C_1$-$C_4$ alkylthio $C_2$-$C_6$ alkenyl.

16. The substituted aminophenylurea derivative of claim 1 wherein R is phenoxy $C_2$-$C_4$ alkenyl.

17. The substituted aminophenylurea derivative of claim 1 wherein R is cyano($C_2$-$C_4$ alkenyl).

18. The substituted aminophenylurea derivative of claim 1 wherein R is $C_2$-$C_4$ alkynyl.

19. A pharmaceutical composition comprising a tumor-inhibiting amount of a substituted aminophenylurea derivative of formula (I) given in claim 1 or a pharmaceutically acceptable acid addition salt thereof and a pharmaceutically acceptable adjuvant.

20. The pharmaceutical composition of claim 19 wherein the substituted aminophenylurea derivative of formula (I) is N-[p-bis($\beta$-chloroethyl)aminophenyl]-N'-($\beta'$-chloroethyl)urea or a pharmaceutically acceptable acid addition salt thereof.

21. The pharmaceutical composition of claim 19 which comprises from about 0.05 to 90% by weight of the substituted aminophenylurea derivative of formula (I) or its pharmaceutically acceptable acid addition salt.

22. The pharmaceutical composition of claim 19 which comprises from about 1 to 60% by weight of the substituted aminophenylurea derivative of formula (I) or its pharmaceutically acceptable acid addition salt.

* * * * *

UNITED STATES PATENT AND TRADEMARK OFFICE
CERTIFICATE OF CORRECTION

PATENT NO. : 4,803,223
DATED : February 7, 1989
INVENTOR(S) : SHOZO KATO

It is certified that error appears in the above-identified patent and that said Letters Patent is hereby corrected as shown below:

Claim 15, line 2 of the claim, "$C_2$-$C_6$" should read --$C_2$-$C_4$--.

Claim 16, line 2 of the claim, "$C_2$-$C_4$" should read --$C_2$-$C_6$--.

Signed and Sealed this

Twenty-ninth Day of August, 1989

Attest:

DONALD J. QUIGG

*Attesting Officer*  *Commissioner of Patents and Trademarks*